(12) United States Patent
Bleiel et al.

(10) Patent No.: US 10,092,517 B2
(45) Date of Patent: Oct. 9, 2018

(54) GELATED MICROPARTICLE SUITABLE FOR ORAL DELIVERY OF THERAPEUTIC PEPTIDES TO THE LOWER INTESTINE

(71) Applicant: Insucaps Limited, Dublin (IE)

(72) Inventors: Sinead Bleiel, Dublin (IE); Sam Maher, Dublin (IE)

(73) Assignee: Insucaps Limited, Dublin (IE)

( * ) Notice: Subject to any disclaimer, the term of this patent is extended or adjusted under 35 U.S.C. 154(b) by 0 days.

(21) Appl. No.: 15/564,576

(22) PCT Filed: May 13, 2016

(86) PCT No.: PCT/IE2016/000005
§ 371 (c)(1),
(2) Date: Oct. 5, 2017

(87) PCT Pub. No.: WO2016/178202
PCT Pub. Date: Nov. 10, 2016

(65) Prior Publication Data
US 2018/0085316 A1    Mar. 29, 2018

(30) Foreign Application Priority Data

May 6, 2015   (GB) ................................ 1507760.5

(51) Int. Cl.
*A61K 38/28* (2006.01)
*A61K 9/16* (2006.01)
*A61K 9/20* (2006.01)

(52) U.S. Cl.
CPC .......... *A61K 9/1658* (2013.01); *A61K 9/1617* (2013.01); *A61K 9/1652* (2013.01); *A61K 9/2077* (2013.01); *A61K 38/28* (2013.01)

(58) Field of Classification Search
CPC .... A61K 38/28; A61K 9/1617; A61K 9/1652; A61K 9/1658; A61K 9/2077
See application file for complete search history.

(56) References Cited

FOREIGN PATENT DOCUMENTS

| CA | 2 878 026 | 1/2014 |
|---|---|---|
| WO | WO 02/094224 | 11/2002 |

OTHER PUBLICATIONS

Bayomi, et al., "Preparation of casein-chitosan miscropheres containing siltiazem hydrochloride by an aqueous coacervation technique", Pharmaceutica Acta Helvetiae, vol. 73 No. 4, pp. 187-192, 1998.

*Primary Examiner* — Alma Pipic
(74) *Attorney, Agent, or Firm* — Cesari and McKenna, LLP

(57) ABSTRACT

A gelated microparticle suitable for delivery intact to the mammalian lower intestine via an oral route comprises a monodispersed matrix formed of at least partially hydrolyzed casein, chitosan, and an active agent, and includes a minor amount of at least one permeation enhancer dispersed throughout the matrix.

18 Claims, 10 Drawing Sheets

A

B

| SAMPLE | Papp (cm/s) | SEM | TTEST (P value) | STATISTICAL NOTE |
|---|---|---|---|---|
| CONTROL | 2.98425 E-06 | 2.40352E-07 | — | — |
| Encaps No TCA/ Vit B12 | 1.60857 E-05 | 5.07181E-06 | 9.79771E-11 | *** |
| Encaps + TCA (10mg) | 1.22023 E-05 | 1.16424E-06 | 2.7264E-12 | *** |
| Encaps + TCA (20mg) | 1.60224 E-05 | 2.64265E-06 | 3.6275E-17 | *** |
| Encaps + TCA (50mg) | 1.03248 E-05 | 3.04289E-06 | 3.5364E-18 | *** |
| Encaps + Vit B12 (10mg) | 1.60857 E-05 | 2.46426-06 | 9.626421E-12 | *** |
| Encaps + Vit B12 (20mg) | 1.402539 E-05 | 2.26426E-06 | 6.325835 E-14 | *** |
| Encaps + Vit B12 (50mg) | 1.85353 E-05 | 5.26575-06 | 4.352645 E-12 | *** |

GELATED MICROPARTICLE SUITABLE FOR ORAL DELIVERY OF THERAPEUTIC PEPTIDES TO THE LOWER INTESTINE

CROSS REFERENCE TO RELATED APPLICATIONS

This application is the National Stage of International Application No. PCT/IE2016/000005, filed on May 13, 2016, which claims the benefit of Great Britain Application No. 1507760.5, filed on May 6, 2015. The contents of both applications are hereby incorporated by reference in their entirety.

TECHNICAL FIELD

The invention relates to a gelated microparticle suitable for oral delivery of therapeutic peptides to the lower intestine. The invention also relates to a method of making the gelated microparticles.

BACKGROUND TO THE INVENTION

Therapeutic peptides are a successful drug class with attributes that often include high potency, good efficacy and low toxicity. There are over 60 peptide drugs licensed for clinical use worldwide. The market for synthetic peptides has grown from $5 billion in 2004 to currently over $13 billion [1]. According to market research, the number of peptides in clinical development is over 100 and in preclinical development is over 400 [2]. The growing success of peptide therapeutics is accentuated by poor stability, low and variable oral bioavailability, rapid plasma clearance and high manufacturing cost relative to conventional small molecules. These limitations often leave industry with no option other than to formulate the peptides in injectable dosage forms, which generates significant manufacturing costs. Reformulation of a peptide into an oral dosage form could reduce the costs associated with sterile manufacture of injectables. However, this depends on the amount of bioactive peptide that is required in the oral dosage form, with concomitant influence upon both the efficiency of the delivery system and the cost to synthesise the therapeutic peptide.

The financial limitations of oral delivery of therapeutic peptides relates to the molecular weight of the peptide in addition to its potency, structural complexity and the frequency of administration. For specialist drug delivery, candidate peptides are carefully selected for reformulation. For example, selecting a complex high molecular weight peptide or protein manufactured by an expensive recombinant approach that subsequently requires repeat daily administration is less likely to be commercially viable in an oral format; given the likelihood that the peptide will have low oral bioavailability. Hence, these financials impediments need to be addressed when choosing the candidate peptides.

In an oral format, insulin for example could be administered earlier in the progression of the diabetes disease. The requirement for needles can, in some cases, reduce patient compliance especially those undergoing treatment for chronic, non-life threatening diseases. Hence, an oral format may improve compliance. From a therapeutic perspective, oral delivery of some peptides can represent a more physiological route compared with injectable formats; since injectable routes can expose diabetics to hyperinsulinemic hypoglycemia [4]. This issues are also imperative for consideration during development of oral delivery systems.

Delivery of a peptide by the oral route could also reduce primary healthcare costs by eliminating the need for skilled professionals to administer certain dosage forms. Improved patient compliance also reduces the requirement for primary intervention. The benefits of delivery by the oral route clearly outweighs delivery by the parenteral route, which is reflected in the fact that two thirds of all pharmaceutical dosage forms are oral products [5].

In recently years, a number of oral peptide dosage forms that are based on both novel and established concepts in oral drug delivery have progressed to clinical assessment with varying levels of success. Significant R&D effort has led to a number of oral insulin formulations reaching clinical trial assessment. To date no oral insulin formulation has been licensed for use in the treatment of diabetes. The most advanced oral peptide formulations in clinical development are solid dosage formulations consisting of conventional admixed solids used in the preparation of enteric coated tablets. Despite such a plethora of research, there are few disclosures that address the mode of dose delivery and design for oral insulin, and hence development issues related to development of solid dosage forms are yet to be addressed.

The main peptides in clinical development include glucagon like peptide-1 (GLP-1), insulin and exenatide, salmon calcitonin (sCT), octreotide, parathyroid hormone (PTH), and human growth hormone (hGH) as well as the polysaccharide drug, low molecular weight heparin (LMWH). In the majority of cases, oral peptide formats in clinical development are new formulations of established parenteral therapeutics, and so the success of the oral format does not relate to the drug efficacy specifically; it will, however, it depends on the performance of the new drug delivery system.

The amount of peptide in many of the oral dosage forms is significantly higher relative to those delivered by the parenteral route which is made feasible by more efficient processes for peptide synthesis. Some of the companies developing oral formulations are also publishing patents to improve efficiency of manufacturing (e.g. Biocon, India U.S. Pat. No. 8,058,391). The higher quantity of active in an oral peptide format permits a certain loss of peptide as it negotiates each of the pre-systemic barriers to the circulation. It is clear that the value of peptide bioavailability becomes less important relative to the achievement of safe, efficient reproducibility. This point is further highlighted by the licensed peptide desmopressin (DDVMP, Ferring, Switzerland), one of only two peptides licensed for delivery by the oral route in a formulation with bioavailability of only 0.1%.

From a biopharmaceutics aspect, the key challenges encountered in oral peptide delivery are pre-systemic degradation, poor permeability across the intestinal epithelium and hepatic metabolism. Peptides are susceptible to chemical instability, conformational instability and enzymatic degradation during manufacture processes such as extrusion, pressing or drying, product storage and subsequent absorption and systemic degradation. The bioactivity of a peptide is very quickly lost in the stomach milieu as the harsh acidic condition can reduce tertiary and quaternary disulphide bridges and can also facilitate hydrolysis of intact peptides into shorter inactive sequences. The gastric environment can be avoided by enteric coating with weakly acidic polymer films that delay release by melting above their pKa in a pH dependant fashion.

Drug solubility is however fundamental in oral peptide delivery and significant research has attempted to improve peptide solubility to address this need. The structure activity function of most peptide drugs and their target receptors make it difficult to reduce the number of amino acids that contribute to the amount of hydrogen bond donors in the molecule or the molecular weight or the Log P; not without very substantial structure activity relationship studies. Approaches have included increasing the molecular weight by alkylation via hydrolysable bonds, and while this increases the Log P, it also increases molecular weight.

Hence, the importance of a suitable dosage form capable of facilitating oral peptide delivery is imperative. Despite the concentration of peptide in the dosage form, inadequate protection from degradation or a lack of permeation enhancement of the peptide across the intestinal epithelium will result in failure in both pre-clinical and clinical development.

A significant volume of research has focused on efforts to improve peptide stability and permeation by chemical modification or non-covalent complexation. Structural modification, including the formation of prodrugs, is a successful drug delivery approach that is commonly used to improve the physicochemical properties of drugs, including peptides and proteins. PEGylation, the conjugation of protein with polymers of polyethylene glycol, is a useful way of increasing serum half-life of biotech drugs that are delivered by the parenteral route.

Synthesis of all peptide with D-amino acids can prevent peptide digestion and improve peptide bioavailability. For example, the substitution of two D-amino acids (alanine and leucine) in the pentapeptide enkephalin improved oral bioavailability by over 20-fold when delivered with amistatin orally in rats. In 2005, Biocon acquired Nobex Corp. (USA) and with it the intellectual property for a PEGylated and alkylated oral insulin format called IN-105 (U.S. Pat. No. 5,359,030 U.S. Pat. No. 5,681,811A, U.S. Pat. No. 6,770, 625B2, EP1430082B1 U.S. Pat. No. 6,309,633 B1). Insulin is covalently modified at position B29 with polyethylene glycol using an acyl chain linker, which improves stability of the peptide to proteolysis and reduces mutagenicity without significantly altering the peptides pharmacological activity.

Physical complexation of peptide to a carrier substance is a possible alternative to chemical modification that can improve the lipophilic characteristics of the peptide and in some cases improve the stability of the peptide. Ionic complexation is widely applicable in the formulation of conventional small molecule drugs, to such an extent that it is estimated that 50% of all drugs are formulated as salts.

Furthermore, research also aims to overcome poor efficiency and proteolysis of insulin-$B_{12}$ conjugates (1:1) has resulted in the evaluation of insulin loaded, $B_{12}$ coated nanostructures (Access Pharmaceutical, USA) that protect the peptide from degradation and improve the efficiency of permeation. Another example of this strategic approach involves conjugation of target peptide to modified transferrin leading to more favourable pharmacokinetics (U.S. Pat. No. 8,129,504). However, concerns remain in relation to saturable receptors that can reproducibly improve peptide permeation especially when a wide and varied diet is factored into the study design.

It is an object of the invention to overcome at least one of the above-referenced problems.

STATEMENTS OF INVENTION

The inventors have surprisingly discovered that microparticles having a matrix formed of casein and chitosan has a synergistic inhibitory effect on gastric enzymes (FIG. 2) and a synergistic effect on intestinal adhesion compared with gastric adhesion (FIG. 3). Thus, the microparticles ability to transit the stomach intact and adhere to intestinal mucose is improved. The Applicant has also discovered that inclusion of a permeation enhancer in the matrix improves the transport of [$^{14}$C mannitol] across intestinal mucosa (FIG. 5). Mannitol was chosen as a surrogate active agent as it has a similar size and molecular weight to therapeutic peptides such as insulin.

In a first aspect, the invention provides a gelated microparticle suitable for delivery intact to the mammalian lower intestine via an oral route and comprising a monodispersed matrix formed of at least partially hydrolysed casein, chitosan, and an active agent, and including a minor amount of at least one permeation enhancer dispersed throughout the matrix.

In another aspect, the invention provides a gelated microparticle suitable for delivery intact to the mammalian lower intestine via an oral route and comprising a monodispersed matrix formed of at least partially hydrolysed casein and/or chitosan, and an active agent, and typically including a minor amount of at least one permeation enhancer dispersed throughout the matrix.

Preferably, the at least one permeation enhancer is selected from TCA and Vitamin B12. The combination of TCA with chitosan was shown to provide excellent permeation enhancement compared with other permeation enhancers (FIG. 9a and FIG. 11). Addition of 10, 25 and 50 mg of TCA to the encapsulation system reduced TEER and increased mannitol permeability by 5-8- and 11-fold to within the order of $10^{-5}$ cm/s, a coefficient range that is often observed with substances that have good permeability. Surprisingly, the presence of vitamin B12 assists with peptide transport via receptor mediated endocytosis (e.g. vitamin $B_{12}$ receptor) (FIG. 9b and FIG. 10). Vitamin B12 significantly reduced TEER over 2 hours with additional enhancement of mannitol flux demonstrating 11.5-fold increase at 25 mg concentrations in encapsulation systems. Receptor mediated delivery of a peptide loaded through the use of vitamin $B_{12}$ receptors represents an attractive alternative to direct conjugation as it protects the therapeutic peptide and improves the efficiency of permeation.

In one embodiment, the active agent is a low molecular weight therapeutic agent.

Ideally, the at least one permeation enhancer comprises TCA and Vitamin B12.

Preferably, the low molecular weight therapeutic agent is a therapeutic peptide.

In one embodiment, the microparticle comprises 50-80% casein (w/w).

In one embodiment, the microparticle comprises 68-75% casein (w/w).

In one embodiment, the microparticle comprises 1-5% chitosan (w/w).

In one embodiment, the microparticle comprises 2-4% chitosan (w/w).

In one embodiment, the microparticle comprises 20-40% active agent (w/w).

In one embodiment, the microparticle comprises 24-35% active agent (w/w).

In one embodiment, the microparticle comprises 0.001-0.1% permeation enhancer (w/w).

In one embodiment, the microparticle comprises 0.001-0.1% permeation enhancer (w/w).

In one embodiment, the microparticle comprises 0.005-0.02% TCA (w/w).

In one embodiment, the microparticle comprises 0.02-0.06% Vitamin B12 (w/w).

Typically, the gelated microparticle comprises:
at least 50-80% casein (w/w);
at least 3% chitosan (w/w); and
at least 20-40% active agent (w/w).

Preferably, gelated microparticle comprises:
68-75% casein (w/w);
5-8% chitosan (w/w); and
24-35% active agent (w/w).

More preferably, the gelated microparticle comprises:
68-75% casein (w/w);
5-8% chitosan (w/w);
24-35% active agent (w/w);
0.005-0.02% TCA (w/w); and
0.02-0.06% Vitamin B12 (w/w).

The invention also provides a gelated microparticle of the invention in a dried format.

The invention also provides a solid oral dosage form comprising gelated microparticles of the invention.

The invention also provides a directly compressed tablet comprising gelated microparticles of the invention in combination with at least one pharmaceutic excipient.

The invention also provides a pharmaceutical agent comprising gelated microparticles of the invention in combination with a suitable pharmaceutical carrier.

In a second aspect, the invention relates to a method of making a gelated microparticle comprising an active agent and suitable for delivery of the active agent intact to the mammalian lower intestine via an oral route, the method comprising the steps of:
  providing a solution of partially hydrolysed casein and chitosan in a suitable solvent in which the partially hydrolysed casein is negatively charged and the chitosan is positively charged;
  adding the active agent and permeation enhancer to the solution to provide a microdroplet-forming solution;
  extruding the microdroplet-forming solution through a device to form microdroplets;
  immersing the microdroplets in an acidification bath to form gelated microdroplets; and
  optionally, drying the gelated microdroplets.

Typically, the microdroplet-forming solution is extruded through a jet cutter device to form the microdroplets.

In one embodiment, the invention includes an initial step of preparing separate casein and chitosan solutions, mixing the separate solutions to provide a composite solution, and then heating the composite solution to provide the solution of partially hydrolysed casein and chitosan in which the partially hydrolysed casein is negatively charged and the chitosan is positively charged.

Preferably, the microdroplet-forming solution comprises 20-30% casein (w/v) and 1-5% chitosan (w/v).

The invention also relates to a gelated microparticle of the invention (or pharmaceutical or oral dosage form comprising gelated microparticles of the invention) for use in a method of treating diabetes in a mammal, in which the gelated microparticles of the invention comprise a therapeutically effective amount of insulin or an insulin analog, optionally in combination with an insulin sensitizing agent.

Definitions

"Gelated microparticle" means a particle having an average dimension of 10-250 microns as determined by electron microscopy that is initially formed as a liquid microdroplet which is immediately immersed in a gelation bath to form the gelated microparticle.

"Suitable for delivery intact to the mammalian lower intestine via an oral route" means that the microparticle when delivered orally is capable of surviving gastric transit and being delivered to the lower intestine substantially intact.

"Monodispersed matrix" means that the components of the microparticle are homogenously mixed in a single phase. This is distinct from microcapsules having a core-shell morphology. In a monodispersed matrix, all of the components are exposed on the surface and available to interact with their environment to provide a functional benefit.

"Casein" means dairy casein protein. It can be provided as a casein powder such as sodium caseinate, or a dairy-milk derived powder or liquid containing 15-85% casein by weight of total protein. An example of a dairy-milk derived powder is skim milk powder, and an example of a dairy-milk derived liquid is UHT milk. Preferably, the source of casein comprises at least 50%, preferably at least 60%, preferably at least 70%, and preferably at least 80% casein by weight of total protein in the casein source.

"Partially hydrolysed casein" means casein protein that has been partially hydrolysed to break up at least some of the proteins into smaller polypeptides thereby facilitating subsequent gelation when the microdroplets are immersed in a gelation bath. The degree of hydrolysis is variable and can be determined by routine experimentation. Typically, the casein is hydrolysed to a degree of hydrolysis of from 20 to 78% hydrolysis as determined using a method of (Hydrolysis of proteins performed at high temperatures and for short times with reduced racemization, in order to determine the enantiomers of D- and L-amino acids, Csapo, J. et al., *Acta Univ. Sapientiae, Alimentaria,* 2008; pg 31-48). Methods of hydrolysis will be known to a person skilled in the art, and include thermal and proteolytic hydrolysis. In one embodiment, the casein is hydrolysed at 80-90° C. for 10-20 minutes. It will be appreciated that the same degree of hydrolysis can be achieved at lower temperature for longer periods.

"Chitosan" is an art-recognised term and for the purpose of this specification includes natural chitosan (Poly-(D) glucosamine) and chitosan derivatives including trimethyl chitosan, dimethylethyl chitosan, triethyl chitosan. Chitosan does not require hydrolysis—however, sterilisation, typically at 121° C. for 15 minutes is preferred. Thus, ideally, the chitosan is sterilised (i.e. subject to a commercial sterilisation process).

"Permeation enhancer" means a molecule capable of enhancing the transport of insulin across the intestinal epithelium. In one embodiment, the term means a molecule that is capable of enhancing the transport of [$^{14}$C]-mannitol from the apical side to the basal side of a section of rat intestinal tissue using an Ussing Chamber, as described below. Examples of permeation enhancers suitable for enhancing transport across intestinal epithelium will be known to those skilled in the art and include bile salts. In one embodiment of the invention, the permeation enhancer is selected from a bile acid and Vitamin B12. In one preferred embodiment, two permeation enhancers are employed, namely Taurocholic acid (TCA) and Vitamin B12, or derivatives thereof.

"Minor amount" as applied to permeation enhancer means less than 1% (w/w) of dry microparticle, and preferably less than 0.1% (w/w) of dry microparticle.

"Active agent" means a drug or pharmaceutically active agent intended to be delivered into the mammalian body in an oral dosage form and via the intestinal epithelium. In one embodiment, the active agent is a low molecular weight therapeutic having a MW of less than 20 KDa, preferably less than 15 KDa, and ideally less than 10 KDa. In one embodiment, the active agent is a therapeutic peptide or a low molecular weight heparin.

"Therapeutic peptide" means a pharmaceutically active peptide (or analog or conjugate comprising a therapeutic peptide) that is generally hydrophobic and insoluble in water and conventionally delivered by means injection. Examples will be known to those skilled in the art, and include insulin, exenitide, GLP-1, salmon calcitonin (sCT), octreotide, parathyroid hormone (PTH), and human growth hormone (hGH). The term peptide typically means a polymer composed of up to 50 amino acid monomers via peptide bond linkage. These peptides can be prepared by conventional methods, i.e., chemical synthesis or recombinant technology. When necessary, any of the peptides employed in the invention can be chemically modified to increase their stability. A chemically modified peptide or a peptide analog includes any functional chemical equivalent of the peptide characterized by its increased stability and/or efficacy in vivo or in vitro in respect of the practice of the invention. The term peptide analog also refers to any amino acid derivative of a peptide as described herein. A peptide analog can be produced by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NABH_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

"Insulin analog" means a molecule that mimics the effects of insulin in-vivo. Many analogs are described in the literature including exenitide, arylalkylvanadium salts, selenium, alpha lipoic acid to name but a few.

"Bile acid" means a steroid acid found predominantly in the bile of mammals. The term excludes bile salts, which are bile acids conjugated with taurine or glycine. Examples of bile acids include cholic acid derivatives, for example taurocholic acid (TCA) and glycocholic acids, and chenodeoxycholic acid derivatives, for example taurochenodeoxycholic acid and clycochenodeoxycholic acid derivatives. Some examples of bile acids are shown in FIG. 13.

"TCA" means taurocholic acid. Preferably, the TCA is a medium viscosity TCA having a molecular weight of 300-400 KDa, ideally about 350 KDa.

"Vitamin B12" means a cobalamin and cobalamin derivatives, such as cyanocobalamin, hydroxycobalamin, methylcobalamin, adenosylcobalamin. Generally, the Vitamin B12 comprises a planar tetra-pyrollole and complexed cobalt.

"(w/w)" means dry weight, i.e. weight of component X as a % of total weight of microparticle dried to a water activity (Aw) of 0.20.

"Water activity (Aw)" The water activity (Aw) of a food/ingredient is the ratio between the vapour pressure of the ingredient itself, when in a completely undisturbed balance with the surrounding air media, and the vapour pressure of distilled water under identical conditions. The most common method used to measure water activity is the Equilibrium Relative Humidity equation (ERH), which is expressed in percentage or as the water activity expressed as a decimal. A portion of the total water content present in food is strongly bound to specific sites and does not act as a solvent. These sites include the hydroxyl groups of polysaccharides, the carbonyl and amino groups of proteins, and others on which water can be held by hydrogen bonding, by ion-dipole bonds, or by other strong interactions. This binding action is referred to as the sorption behavior of the food. The most successful method for studying the sorption properties of water in food products has been the preparation of "Sorption Isotherms," or curves relating the partial pressure of water in the food to its water content at constant temperature. The same practice is followed to study curves relating water activity under equilibrium conditions to water content.

Food of known moisture content is allowed to come to equilibrium with a small headspace in a tight enclosure and partial pressure of water activity is measured manometrically, or relative humidity is measured using a hydrometer. Water activity is equal to equilibrium relative humidity divided by 100:

$$Aw=ERH/100$$

... where ERH is the equilibrium relative humidity (%).

Relative humidity sensors of great variety are available for this purpose, including electric hygrometers, dewpoint cells, psychrometers, and others.

"Dried format" means that the microparticle is dried to a water activity (Aw) of less than 0.40, preferably less than 0.30, and more preferably about 0.20 as determined using the method and equation related to the Equilibrium. Relative Humidity (ERH), which is expressed in percentage or as the water activity expressed as a decimal.

"Oral dosage form" means a dosage form suitable for oral delivery. Examples include tablets, pills, capsules, powders, granules, flakes and the like. "Solid oral dosage form" means a tablet, pill or capsule that may be formed by direct compression and may include direct compression excipients such as DC mannitol and disintegrants or superdisintegrants, flavouring agents. A composition for oral administration can be any orally acceptable dosage form including capsules, tablets, emulsions, and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A pharmaceutically acceptable carrier is routinely used with one or more active above-mentioned compounds. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an above-mentioned compound. Examples of other carriers include colloidal silicon oxide, magnesium stearate, cellulose, sodium lauryl sulfate, and D&C Yellow #10.

"Suitable solvent" typically means a buffered solution having a pH at which casein is negatively charged and chitosan is positively charged, thus allow the casein and chitosan interact to form microparticles. Generally, a solvent having a pH of 6-7 ensures that the charges of the casein and chitosan is correct, ideally about 6.5. In one embodiment, the casein and chitosan are solubilised separately before being combined.

"Casein solution": In one embodiment, the casein is first solubilised in water at a pH of 7-9, preferably about 7.5-8.5, and ideally about pH of 8. In one embodiment, 20-30% casein is employed, preferably 22-26%, and ideally about 24% (w/v). In one embodiment, the casein is solubilised for a period of at least 12 hours, preferably at least 18 hours, and ideally about 24 hours.

"Chitosan solution": In one embodiment, the chitosan is first solubilised in a weak acid, for example acetic acid or citric acid, preferably 0.005-0.02% weak organic acid. In one embodiment, 1-5% chitosan is employed, preferably 2-4%, and ideally about 3% (w/v). In one embodiment, the chitosan is de-aerated for a period of at least 12 hours, preferably at least 18 hours, and ideally about 24 hours.

"Extruding through a device" means passing the microdroplet-forming solution through a device which breaks the solution into microdroplets. Examples of suitable devices include nozzles including vibrating nozzles, spray dryers, jet cutters, and rotating disc cutters, electrostatic extrusion. Jet cutters are described in Vorlup and Bredford [47].

"Acidification bath" means a bath that is buffered to a pKa of about 4-5, preferably about 4.7 to 4.8. In one embodiment, the bath comprises an organic acid buffer, preferably a citric acid buffer. In one embodiment, the organic acid buffer has a concentration of 0.4-0.8M, preferably 0.5-0.7M, and ideally about 0.6M.

"Weak acid" means an acid that only partially disassociated in water, for example acetic acid or carbonic acid.

DETAILED DESCRIPTION OF THE INVENTION

Figure 1:
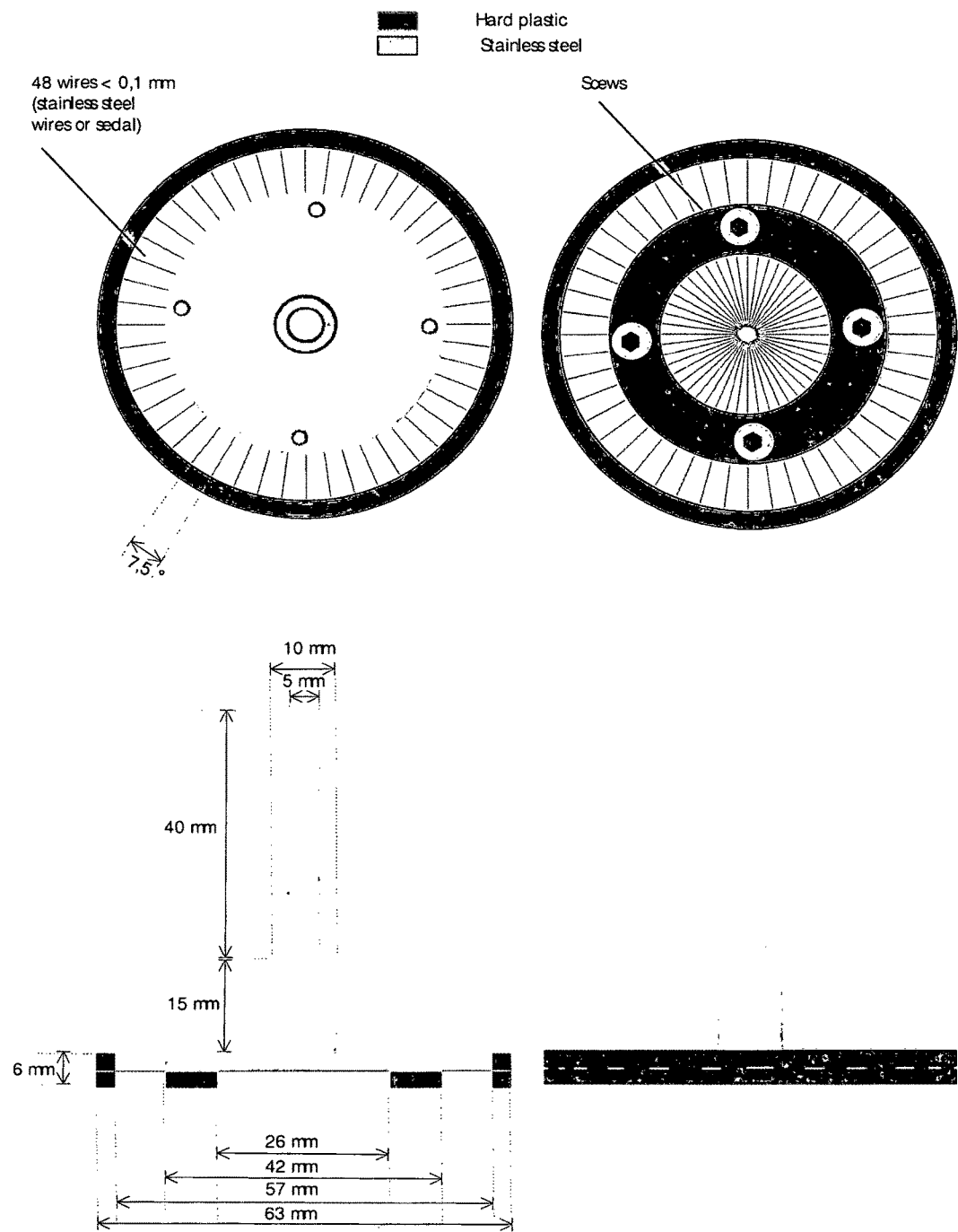
FIG. 1. Jet Cutter Technology used to polymerise polymeric materials for peptide encapsulation.

Methods
Materials
Sodium Caseinate (NaCas) and Chitosan (>90% dry matter basis, 350 kDa) was obtained in addition to Blue Dextran (BD) and Vitamin $B_{12}$ (cyanocobalamin).

Preparation of Polymeric Solutions
Sodium caseinate (NaCas; 24%, w/w total solids) in de-ionized water and permitted to fully hydrate for 24 hours at room temperature. The dispersion was adjusted to desired pH 8.0 (with HCl 1M or NaOH 1M).

Chitosan was prepared (3.0% w/w) in 0.01% acetic acid and was allow to de-aerate for 24 hours at refrigerated temperature.

Both NaCas and Chitosan were mixed in order to achieve a final protein concentration of 11% w/w and final Chitosan concentration of 1.5% w/w).

Final pH was adjusted to pH 6.5 (with HCl 1M or NaOH 1M)

Thermal hydrolysis at 85 Deg C. was conducted under agitation for 15 minutes.

The dispersion was cooled to 37 Deg C. and Taurocholic Acid (TCA) is admixed to achieve a final concentration of 3500 mg TCA in the final mixture The dispersion was then cooled to 30 Deg C.

Dispersion 20 mg/ml insulin with 10 mg/mL cyanocobalamin (2:1 ratio) in 0.01M HCL and disperse in the aforementioned mixture The dispersion is extruded through a jet-cutting rotating disk process.

Microparticles descended and polymerized in a citric acid buffer 0.6M pKa 4.76.

Polymerised micro-particles were recovered after 35 min under gentle stirring

Microparticles of 20-100 microns were generated.

Microparticles were vacuum dried at 30 Deg C. until water activity (Aw) 0.20 was achieved Tests & Results i) Microparticle Permeability Method Blue Dextran, (BD) was added into the NaCas-Chitosan-B12-TCA mixture (ratio 1:25) and BD-loaded microparticles were passed through the jet cutter system as described above.

BD-loaded microparticles were suspended in 1 mL of DMEM and added to apical compartment (n=3). Same protocol was realized with equivalent amount of free BD.

Apparent permeability coefficient (Papp) was calculated:

$$Papp(\text{cm·s-1}) = (dQ/dt) \times [1/(A \cdot C0)] \quad \text{(EQUATION 1)}$$

with dQ/dt, flux of BD across the monolayer (mol/sec), C0

BD initial concentration in the apical compartment (mol/mL), and A, surface area of the monolayer (3.14 cm$^2$).

Comments:

BD (2000 kDa) is a molecule generally used as a paracellular marker. The transport of BD was increased significantly (R=1.98) by loading with NaCas-Chitosan-B12-TCA microparticles (Table 1). This result corresponded well with the TEER values, where a decrease of TEER was observed. Hence, NaCas-Chitosan-B12-TCA microparticles were able to facilitate paracellular transport via tight cell junction opening. This illustrates a statistical significance (p<0.01) between free BD and BD encapsulated in NaCas-Chitosan-B12-TCA microparticles. This represents the potential to transport therapeutic peptides via tight junction openings.

TABLE 1

Transport permeability of BD, free & encapsulated, through Caco-2 cells (p < 0.01).

| Sample | Cumulative Transport of BD | | Papp | |
|---|---|---|---|---|
| | ug | % | (×10$^{-5}$ cms$^{-1}$) | R |
| Free BD | 2.04 ± 0.24 | 0.11 ± 0.03 | 0.071 ± 0.01 | 1.001 |
| BD encapsulated in microparticles | 5.16 ± 0.09 | 0.48 ± 0.01 | 0.164 ± 0.00 | 1.97 | ii) Investigate the Inhibitory Effect on Proteolytic Enzymes (Trypsin/α-Chymotrypsin)

Method

NaCas-Chitosan-B12-TCA microparticles were dispersed (1% w/w) in 1 mL phosphate buffer (0.3 M, pH 7.5) and 1 mL BAPNA (Nbenzoyl dl-arginine p-nitroanilide, 20 mM, Sigma®). Trypsin solution (30 UI) from bovine pancreas (Fisher Scientific) were added at 37° C. This evaluation was focused on typsin inhibition NaCas-Chitosan-B12-TCA microparticles were further dispersed (1% w/w) in 1 mL Tris-HCl buffer (pH 7.8) and 1 mL BTPNA (N-benzoyl-Ltyrosine p nitroanilide, 1.18 mM, Sigma®). Alpha-chymotrypsin (40 UI) from bovine pancreas (Sigma®) were added at 37° C.

After 45 min, enzymatic reactions were stopped with 1% trichloroacetic acid solution and metabolite p-nitroanaline formed was quantified at 405 nm.

Figure 2:
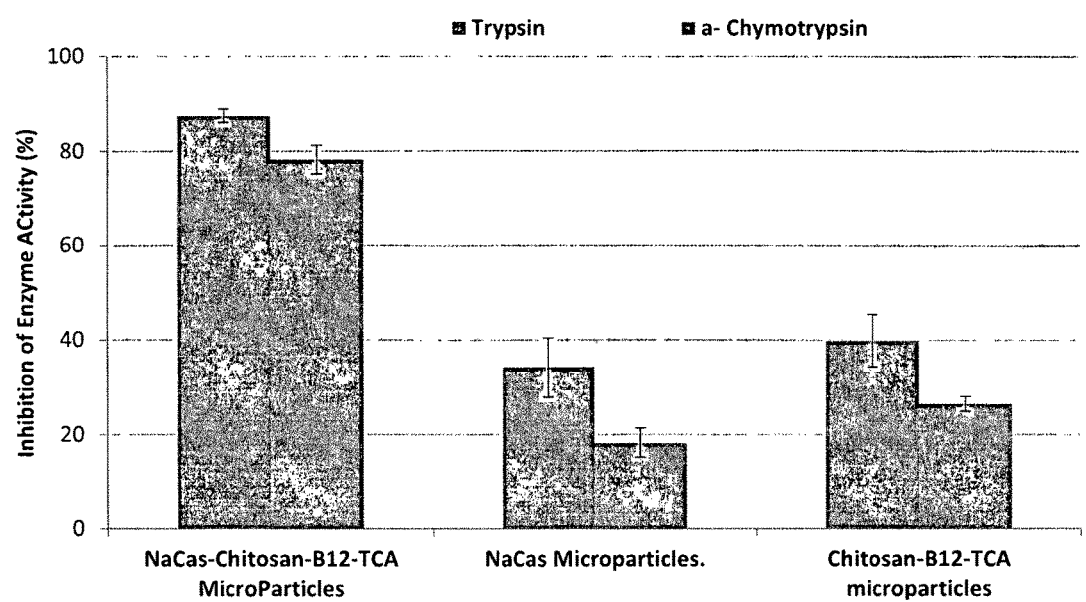
FIG. 2. Rate of enzymatic inhibitory effect of NaCas-Chitosan-B12-TCA microparticles on trypsin and α-chymotrypsin activity ($p<0.05$) relative to NaCas microparticles or Chitosan particles (n=6).

Comments:

NaCas-Chitosan-B12-TCA microparticles inhibited 87.55%±1.43% of trypsin activity and 78.26%±3.09% of α-chymotrypsin activity after 45 min incubation. This inhibitory effect is significantly better relative to NaCas microparticles and Chitosan-B12-TCA microparticles. Hence, the efficacy of NaCas-Chitosan-B12-TCA microparticles was significantly higher than individual element of the formulation. This demonstrates the synergistic effect of the components in the formulation (FIG. 2)

iii) Ex-Vivo Muco-Adhesion Test

Method:

Porcine stomach and intestine were removed under anesthesia and stuck into a Petri dish Thirty microparticles (NO, n=15) were placed onto animal tissue.

The Petri dish was attached to a USP disintegrating apparatus and the number of microparticles adhering to the tissue after 120 min (N) in 900 mL pH 1.2 or pH 6.8 USP buffer were followed to calculate:

$$\% \text{ adhesion} = (N0 - Nt)/N0 \times 100 \quad \text{(EQUATION 2)}$$

Figure 3:
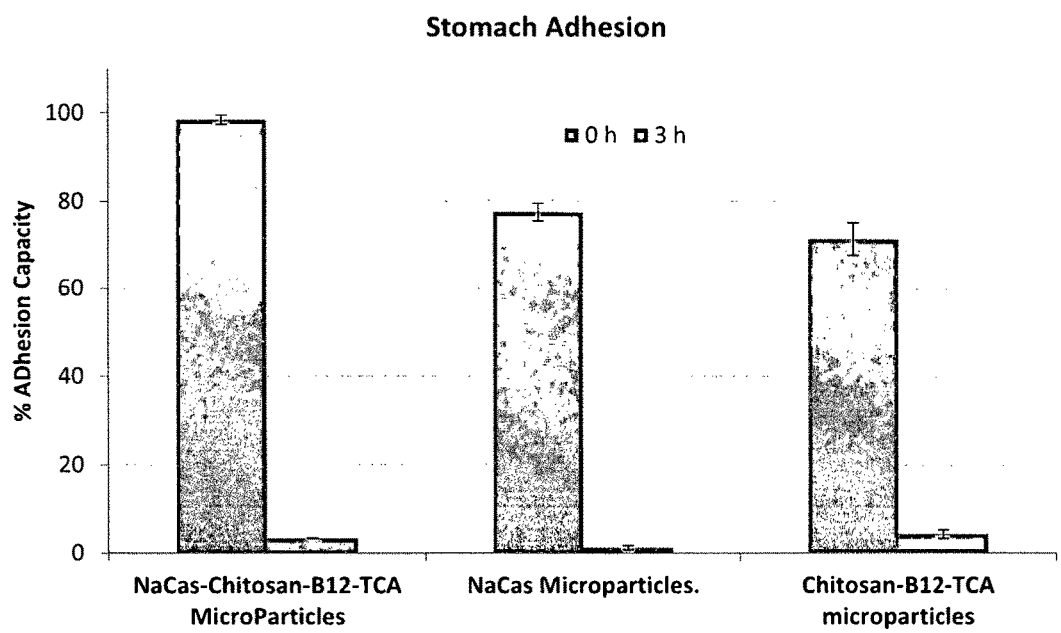
FIG. 3. Rate of bioadhesion of NaCas-Chitosan-B12-TCA microparticles in porcine stomach (A) and intestine (B) ($p<0.05$, n=6), relative to NaCas and chitosan microparticles (n=6).
Figure 3:
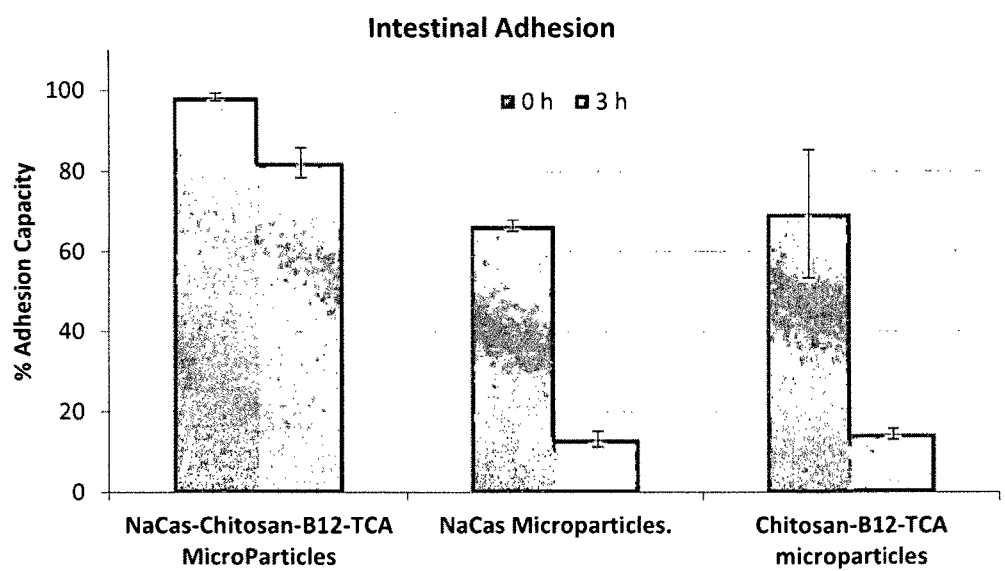

Comments:

After 3 hour incubation, NaCas-Chitosan-B12-TCA microparticles exhibited significant adhesion (82.2%±1.43%) to porcine intestine but no significant adhesion was recorded for the gastric tissue (FIG. 3b). Adhesion capacity of NaCas-Chitosan-B12-TCA microparticles was significantly greater than individual element of the formulation since NaCas and Chitosan microparticles failed to demonstrate effective adhesion capacity (FIG. 3b).

iv) Evaluation of Cyto-Compatibility for Effect on Paracellular Transport

Method:

NaCas-Chitosan-B12-TCA microparticles (n=15) were prepared as outlined above

Digested mixtures were diluted 1/2 with cell culture medium DMEM were added to the apical side of Caco-2 cells (passage 40-45).

The transepithelial resistance (TEER) was followed at defined times up to 2 h and 48 h after polymer removal.

Viability of cells was evaluated by trypan blue exclusion (final concentration 0.15%).

Comments:

Caco-2 cells viabilities were maintained 98.5%-100% and superior to 95% after contact time of 2 h (data not shown). Thus, NaCas-Chitosan-B12-TCA digested microparticles were considered to have a good biocompatibility.

v) Effect of Permeation Enhancer Panel on TEER and Papp of [$^{14}$C]-Mannitol

Ussing Chambers allow the measurement of transport molecules from the apical side of a section of intestinal tissue (rodent) to the basolateral, thereby simulating passage across the gut wall in vivo. The permeation enhancers tested were substances that are found without limits on consumption in food or are listed in various National Compendia. Their ability to improve intestinal permeability was testing in isolated rat colonic mucosae by measurement of transepithelial electrical resistance (TEER) and permeability of

[14C]-mannitol. The permeability of the marker molecule, radioactively labelled sugar ([C14]-Mannitol) was calculated by scintillation counting. Permeability of control segments of rat colon maintained low permeability as measured by maintenance of a starting resistance (>70 $\Omega \cdot cm^{-2}$) over the duration of the experiment. Low permeability coefficient (Papp) value ($2.9 \times 10^{-6}$ cm/s$\pm 1.6 \times 10^{-6}$ cm/s (SD) or $\pm 0.3 \times 10^{-6}$ cm/s (SEM)). Papp values of the order of $10^{-6}$ cm/s are poorly permeable as described in the Biopharmaceutics Classification System.

Method:

Electrophysiology in Isolated Rat Intestinal Mucosae

Stripped jejunal or colonic mucosa is mounted in Ussing chambers (WPI, UK) with a circular window area of 0.63 cm2, bathed bilaterally with 5 mL of KH buffer and continuously gassed with 95% O2/5% CO2 at 37° C.

The transepithelial potential difference (PD, mV) is measured in the open circuit configuration after which the tissue is voltage clamped to zero PD by insertion of the required short circuit current (Isc, $\mu A\, cm^{-2}$) by means of an automatic voltage clamp (EVC-4000 amplifier, WPI, UK).

Isc and PD are alternatively monitored by switching to open circuit conditions for 3 s every 30 s using a timer (Pro-4, WPI, UK). Analogue data was digitised with a Powerlab® data acquisition unit and analyzed with Chart® software package (AD instruments, UK).

Following an equilibration period of 45 min, baseline PD and Isc are measured and TEER ($\Omega\, cm^2$) is calculated according to Ohm's law.

Permeability of [14C]-Mannitol

Transport of radiolabelled mannitol from the apical chamber to the basolateral chamber was used to measure intestinal permeability.

Following addition of [$^{14}$C]-mannitol (0.2 µCi) to the apical chamber flux is monitored periodically over two hours by sampling the serosal chamber (100 µL) every 20 minutes for two hours, and apically (100 µL) at time zero, replenishing with fresh KH buffer at each sampling point.

Samples containing [$^{14}$C]-mannitol were mixed with scintillation fluid and read in a scintillation analyzer (Packard Tricarb 2900 TR).

The apparent permeability coefficient ($P_{app}$) for mannitol and FD4 is calculated according to the equation; $P_{app}$ (cm/s)=(dQ/dt) (1/AC$_0$), where dQ/dt is the transport rate (mol/s); A is the surface area of the monolayer (cm$^2$), and C$_0$ is the initial concentration in the donor compartment (mol/mL).

Figure 4:
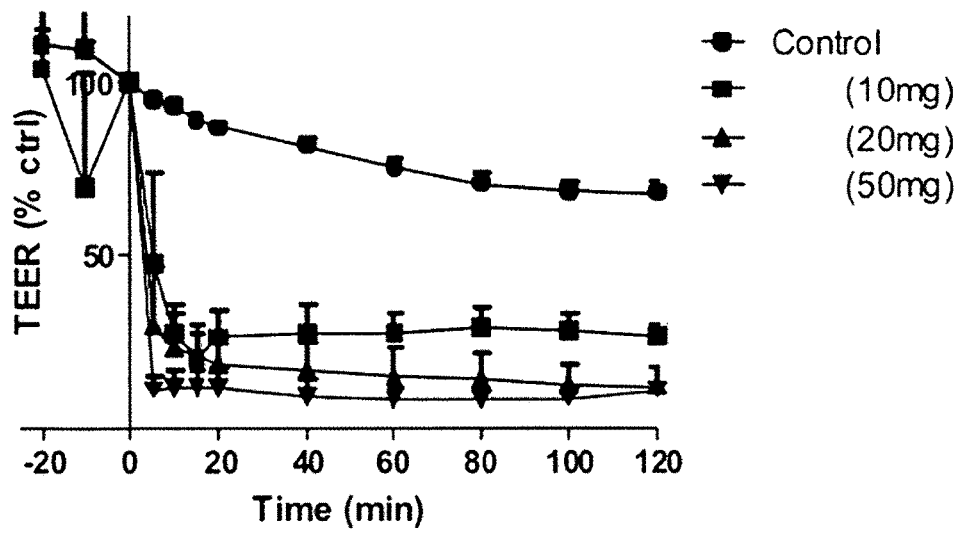
FIG. 4. Effect of NaCas-Chitosan-B12-TCA microparticles on TEER in isolated rat colonic mucosae mounted in Ussing chambers. Legend is NaCas-Chitosan-B12-TCA admixture at different concentrations (n=3).

Comments:

The NaCas-Chitosan-B12-TCA microparticles were digested and presented Ussing chamber using the aforementioned conditions. A concentration- and time-dependent drop in TEER and concurrent increase in mannitol Papp at 2, 4 and 10 mg/mL which correspond to 10, 20, and 50 mg per individual Ussing chamber. Addition of NaCas-Chitosan-TCA microparticle mixtures increased Papp of 14C mannitol by 12-fold to within the order of $10^{-5}$ cm/s, a coefficient range that is often observed with substances that have good permeability (BCS Class I) (FIG. 4). This digested polymerix mixture illustrated the ability to significantly improve permeability (Papp) at the lowest concentration (see FIG. 4).

TCA is a crude bile acid has FDA GRAS status for use as a food additive and supplement. The early hypothesis for the invention related to the permeation enhancing capabilities of TCA to enable the enhanced uptake of peptide such as mannitol and insulin. For this reason, the NaCas-Chitosan-B12-TCA microparticles could be used in delivery of potent pharmaceutical peptides, peptides in food supplements or functional foods. This shows potential that NaCas-Chitosan-B12-TCA microparticles has the potential to deliver therapeutic peptides, with a similar molecular weight to mannitol i.e. insulin.

TABLE 2

Summary of Papp values calculated for each NaCas - Chitosan - TCA admixture screened
(* P < 0.01, P < 0.001, * <0.0001)

| SAMPLE | Papp (cm/s) | SEM | TTEST (P value) | STATISTICAL NOTE |
|---|---|---|---|---|
| CONTROL | 2.89905E−06 | 2.6646252E−07 | — | — |
| NaCas - Chitosan - TCA (10 mg) | 1.88722E−05 | 3.532477E−06 | 1.52008E−15 | *** |
| NaCas - Chitosan - TCA (20 mg) | 2.221877E−05 | 8.8035694E−06 | 1.69323E−12 | *** |
| NaCas - Chitosan - TCA (50 mg) | 2.2422421E−05 | 1.9245329E−06 | 4.55662E−21 | *** | vi) Effect of Polymeric Mixture Response to Carbachol

In order to investigate any possible damaging effects of NaCas-Chitosan-B12-TCA microparticles on intestinal tissue, the tissue was treated with increasing concentrations of carbachol.

Method:

Carbachol Preparations

Carbachol (cch) is muscarinic receptor agonist that stimulates $Ca^{2+}$ dependent chloride secretion through apical chloride channels. The activation of cch leads to an inward short circuit current which is measured through a Delta Isc in electrophysiological measurements. Carbachol induces chloride secretion in health tissue which can be measured as an increase in the negative charge across the tissue.

The ability of tissue to respond to cch indicates that it has retained functionality, a surrogate marker off viability.

The ability of the tissue to generate an inward short circuit current response to serosal addition of the muscarinic agonist, carbachol (0.1-10 µM), is used as a measure of epithelial ion transport function at the experimental endpoint.

Figure 5:
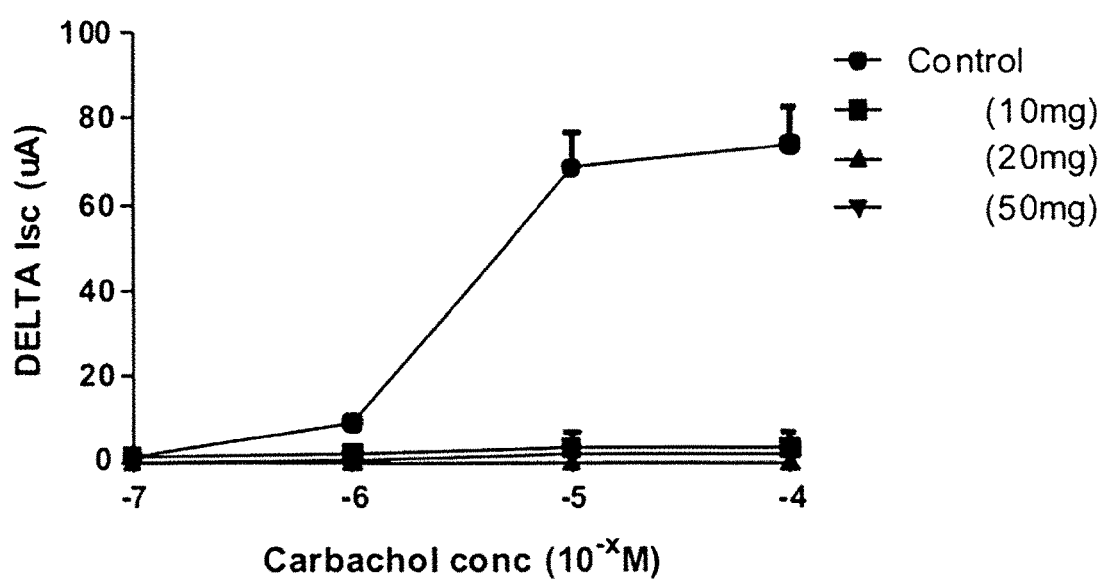
FIG. 5: Effect of NaCas-Chitosan-TCA microparticles on carbachol induced change in electrogenic chloride secretion across isolated rat colonic mucosae as measured by the change in short circuit current (µA). Legend illustrates different concentrations of NaCas-Chitosan-TCA microparticles (n=5).

Comments:

A concentration dependant increase in chloride secretion is seen with the control (FIG. 5) which is typical of healthy tissue. NaCas-Chitosan-B12-TCA microparticles significantly impaired the tissue's ability to respond to carbachol but it does not eliminate it entirely as is seen with other detrimental compounds.

vii) Insulin Detection in Microparticles

Figure 6:
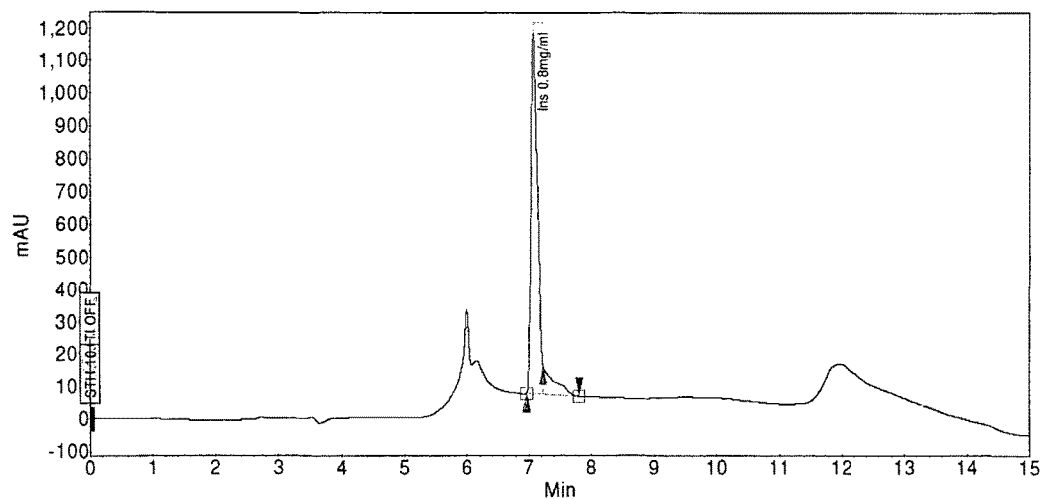
FIG. 6: Chromatogram of insulin 0.9 mg/ml.

A high performance liquid chromatography (HPLC) method was optimised which can detect insulin in the range of 0.8-0.05 mg/ml in NaCas-Chitosan-TCA microparticles and also 5-20 mg/ml in NaCas-Chitosan-TCA microparticles. FIG. 6 is an example of this method and shows insulin eluting at 8 min.

Figure 7:
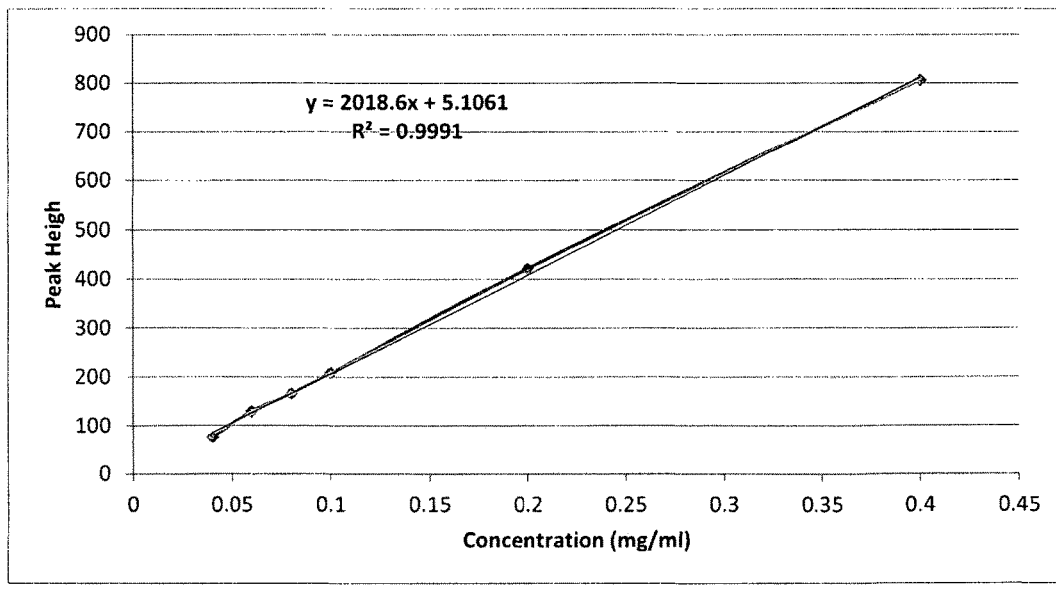
FIG. 7: Insulin standard curve with a linear range of 0.04-0.4 mg/ml. (n=1).
Figure 8A:
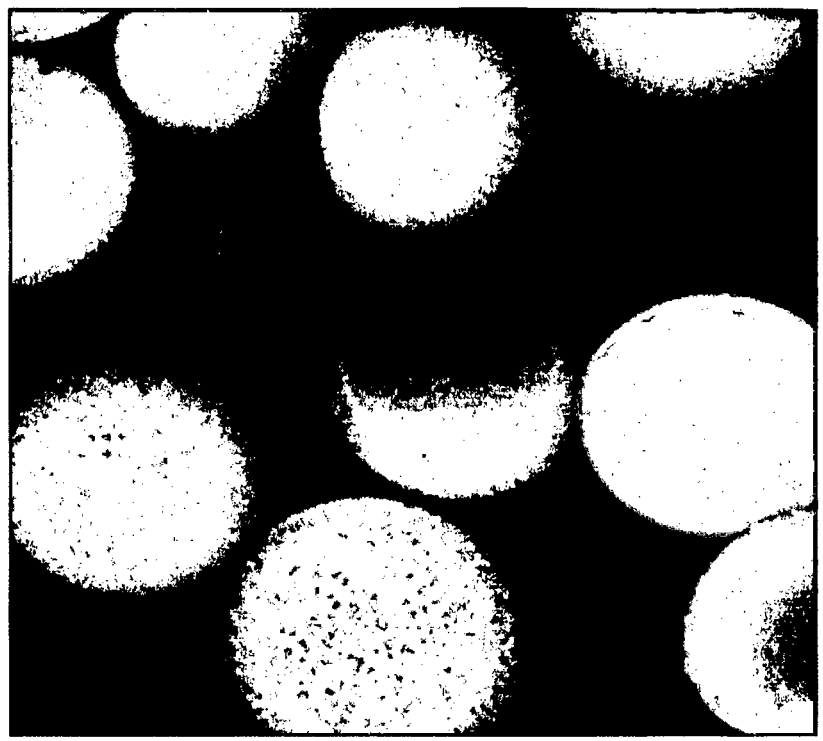
FIG. 8a: Confocal scanning laser microscopy (CSLM) of insulin-loaded pre-drying. Microparticle diameter is approx 180 µm.
Figure 8A:
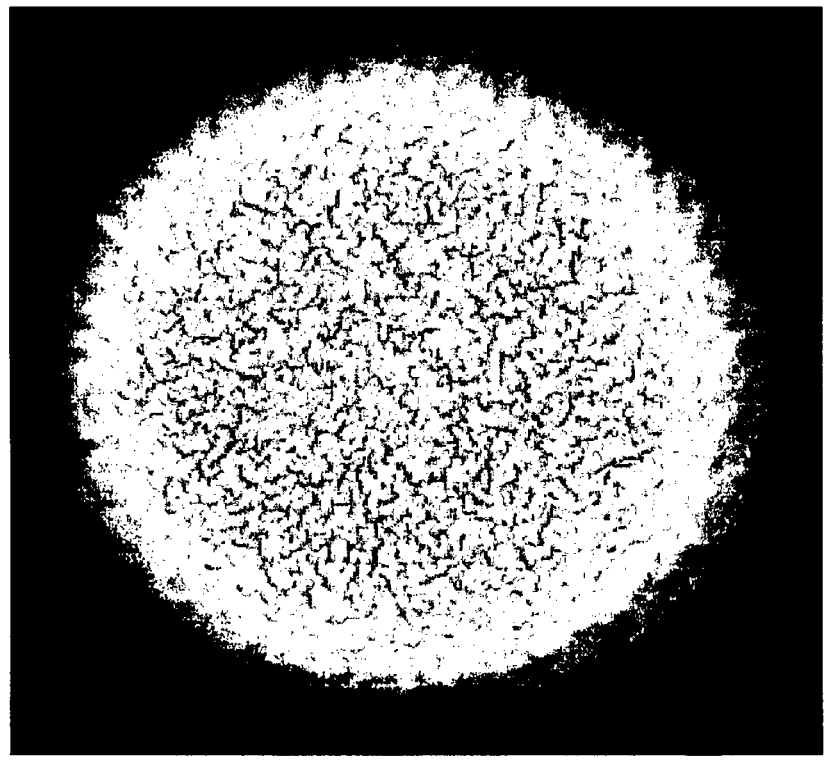
Figure 8B:
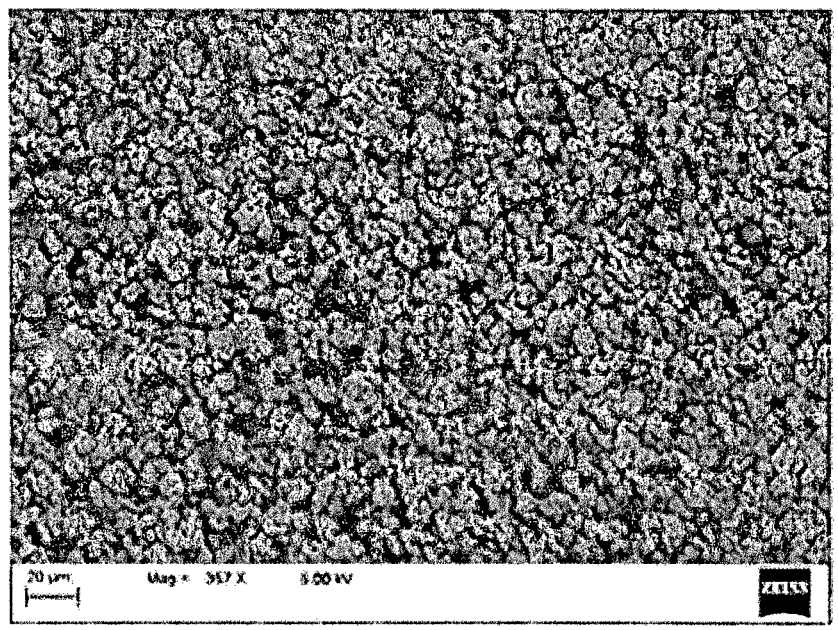
FIG. 8b. Scanning Electron Microscope (SEM) image of insulin-loaded microparticles post-drying. Microparticle diameter is approx. 5 µm (Aw 0.25).
Figure 8B:
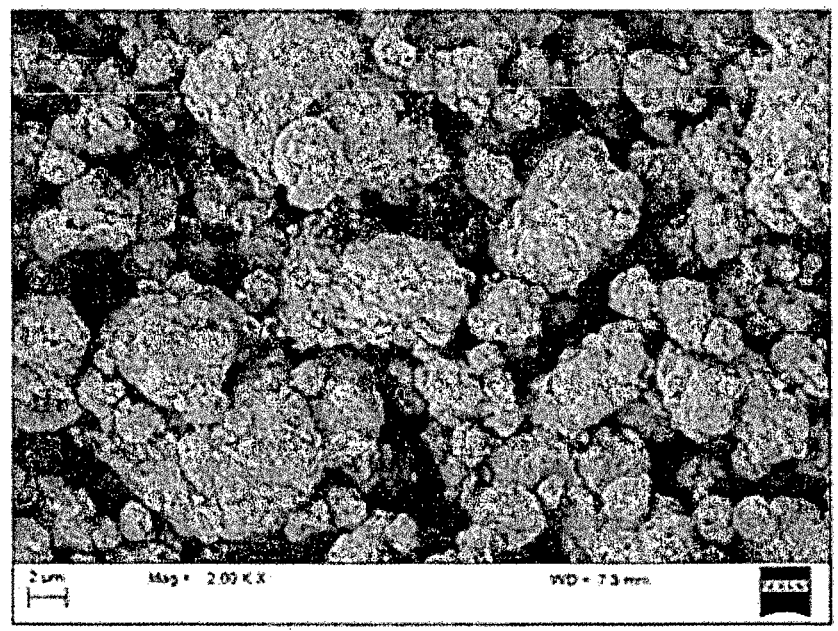

It was later found that this method would need to be optimised further in order to distinguish between insulin and NaCas for the purposes of calculating encapsulation efficiency of insulin in microparticles. FIG. 7 shows the standard curve developed for this method with a linear range of 0.9-0.04 mg/ml.

viii) Solid Dosage Formulation of Minitablets

Method:

Minitablets (50 mg) solid dosage forms are prepared by dry blending NaCas-Chitosan-TCA microparticles and performing direct compression. Each solid was triturated by sieving through a 100 μm wire mesh screen. All additives were then mixed in a sealable vessel and mixed vigorously for 10 minutes at a rate of 60 inversions per minute (5 g of solid suspension yields 100 minitablets). After the sample has settled, all the disintegrant is added and blended at a rate of 60 inversions per minute for 10 minutes. This will ultimately depend on the manufacturer's instruction for direct compression, which is required at laboratory level in the absence of wet granulation or dry granulation (roller compaction).

Figure 9A:
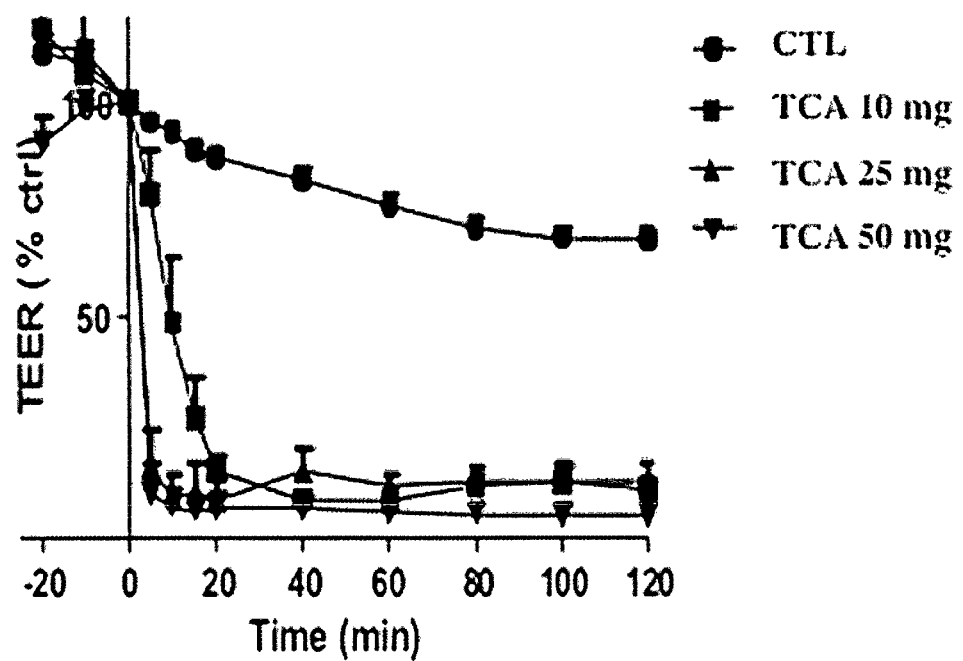
FIG. 9a. Effect of the presence of TCA in the NaCas-Chitosan microparticles on TEER in isolated rat colonic mucosae mounted in Ussing chambers. Legend is NaCas-Chitosan microparticles in the absence of TCA and also in the presence of TCA at different concentrations (n=3).
Figures 9B, 10:
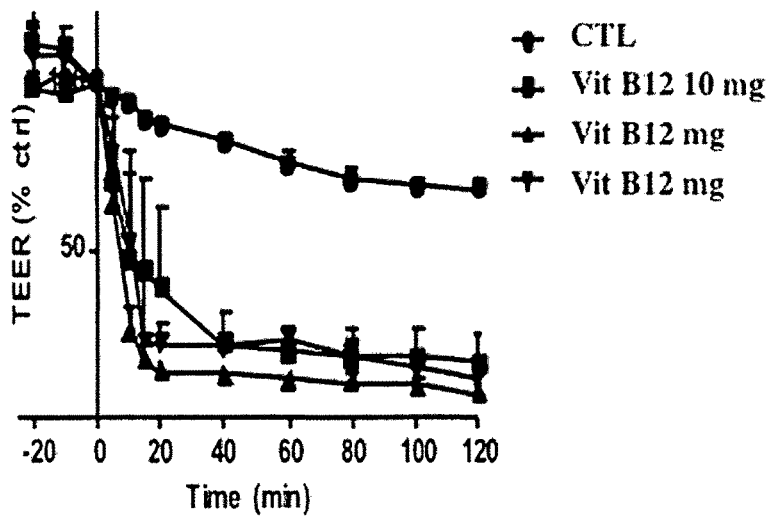
FIG. 9b. Effect of the presence of Vit-B12 in the NaCas-Chitosan microparticles on TEER in isolated rat colonic mucosae mounted in Ussing chambers. Legend is NaCas-Chitosan microparticles in the absence of Vit-B12 in and also in the presence of Vit-B12 in at different concentrations (n=3).
FIG. 10. Summary of Papp values calculated for each permeation enhancer (TCA and VitB12) upon incorporation into NaCas-Chitosan microparticles (*$P<0.01$, $P<0.001$, $<0.0001$).
Figure 11:
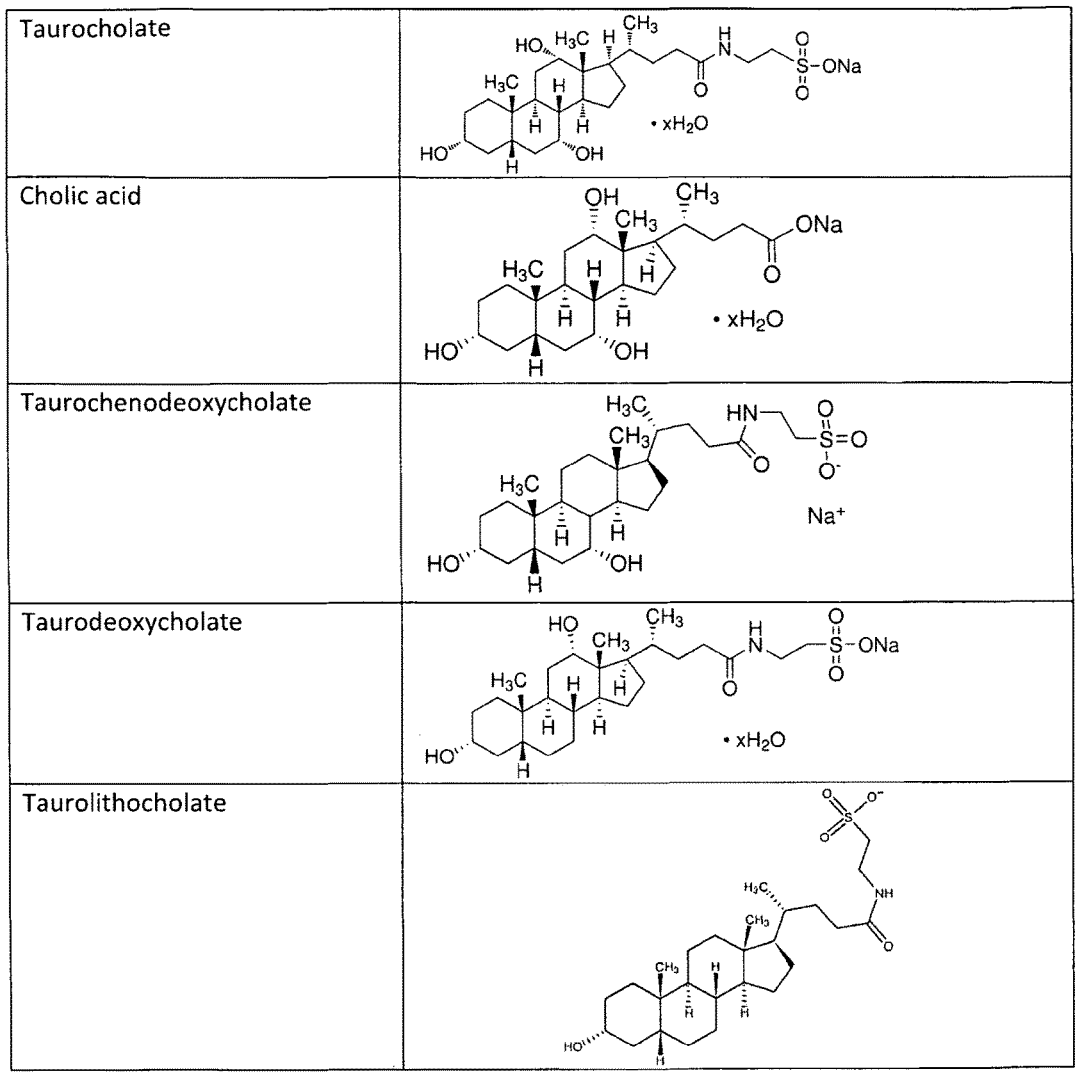
FIG. 11. Bile acid compositional elements

FIG. 9 illustrates the morphology of jet cutter microparticles that are added to the minitablet formulation and FIG. 10 illustrates the microtablets.

REFERENCES

1. Vlieghe, P., et al., *Synthetic therapeutic peptides: science and market*. Drug Discov Today, 2010. 15(1-2): p. 40-56.
2. Lax, R., The Future of Peptide Development in the Pharmaceutical Industry. PharManufacturing: The International Peptide Review, 2010(2): p. 10-15.
3. Owens, D. R., New horizons—alternative routes for insulin therapy. Nat Rev Drug Discov, 2002. 1(7): p. 529-40.
4. Al-Achi, A., Gupta M. R., Stagner W. C., Tablet product design In: Integrated pharmaceutics: applied preformulation, product design, and regulatory science (2013) Wiley pp 215-318.
5. Colon targeting: an emerging frontier for oral insulin delivery. Expert Opinion on Drug Delivery. 10(6): p. 731-739.

The invention claimed is:

1. A gelated microparticle suitable for delivery intact to the mammalian lower intestine via an oral route and comprising a monodispersed matrix formed of at least partially hydrolysed casein, chitosan, and an active agent, and including a minor amount of at least one permeation enhancer dispersed throughout the matrix.

2. A gelated microparticle according to claim 1 in which the at least one permeation enhancer is selected from taurochloric acid and Vitamin B12.

3. A gelated microparticle according to claim 1 in which the at least one permeation enhancer is taurochloric acid.

4. A gelated microparticle according to claim 1 in which the at least one permeation enhancer is Vitamin B12.

5. A gelated microparticle according to claim 1 in which the active agent has a molecular weight of less than 20 KDa.

6. A gelated microparticle according to claim 1 in which the active agent is a therapeutic peptide.

7. A gelated microparticle according to claim 1 in which the microparticle comprises 50-80% casein (w/w).

8. A gelated microparticle according to claim 1 in which the microparticle comprises 1-5% chitosan (w/w).

9. A gelated microparticle according to claim 1 in which the microparticle comprises 20-40% active agent (w/w).

10. A gelated microparticle according to claim 1 in which the microparticle comprises 0.001-0.1% permeation enhancer (w/w).

11. A gelated microparticle according to claim 1 in which the microparticle comprises 0.005-0.02% taurochloric acid (w/w).

12. A gelated microparticle according to claim 1 in which the microparticle comprises 0.02-0.06% Vitamin B12 (w/w).

13. A gelated microparticle according to claim 1 and comprising:
    50-80% casein (w/w);
    at least 3% chitosan (w/w); and
    20-40% active agent (w/w).

14. A gelated microparticle according to claim 1 and comprising:
    68-75% casein (w/w);
    5-8% chitosan (w/w); and
    24-35% active agent (w/w).

15. A gelated microparticle according to claim 1 and comprising:
    68-75% casein (w/w);
    5-8% chitosan (w/w);
    24-35% active agent (w/w);
    0.005-0.02% TCA (w/w); and
    0.02-0.06% Vitamin B12 (w/w).

16. A gelated microparticle according to claim 1 in a dried format.

17. A pharmaceutical composition comprising a gelated microparticle according to claim 1 in combination with a suitable pharmaceutical excipient.

18. A pharmaceutical composition comprising a gelated microparticle according to claim 1 in combination with a suitable pharmaceutical excipient and in which the active agent is insulin or an insulin analog, and in which the at least one permeation enhancer is taurochloric acid, Vitamin B12, or a mixture of taurochloric acid and Vitamin B12.

* * * * *